US008911634B2

(12) United States Patent
Owens et al.

(10) Patent No.: US 8,911,634 B2
(45) Date of Patent: Dec. 16, 2014

(54) APPARATUS AND METHOD FOR SEPARATING MATERIALS OF DIFFERENT DENSITIES

(75) Inventors: Windsor Owens, San Francisco, CA (US); Andrew Peterson, San Francisco, CA (US); Yuri Osipchuk, Foster City, CA (US); Edward Verdonk, San Jose, CA (US)

(73) Assignee: Molecular Devices, LLC, Sunnyvale, CA (US)

( * ) Notice: Subject to any disclaimer, the term of this patent is extended or adjusted under 35 U.S.C. 154(b) by 97 days.

(21) Appl. No.: 13/569,129

(22) Filed: Aug. 7, 2012

(65) Prior Publication Data

US 2014/0045206 A1  Feb. 13, 2014

(51) Int. Cl.
*B01D 33/15* (2006.01)
(52) U.S. Cl.
USPC .......................................... 210/781
(58) Field of Classification Search
USPC .......................................... 210/781
See application file for complete search history.

(56) References Cited

U.S. PATENT DOCUMENTS

| 3,219,266 | A | 11/1965 | Wagman |
| 5,387,174 | A | 2/1995 | Rochat |
| 7,270,730 | B2 | 9/2007 | Schroeder et al. |
| 7,322,926 | B2 | 1/2008 | Due et al. |
| 7,947,186 | B2 * | 5/2011 | Soares et al. .................. 210/782 |
| 8,048,289 | B2 | 11/2011 | Finkel |
| 2005/0054506 | A1 | 3/2005 | Bradley |
| 2007/0267360 | A1 * | 11/2007 | Pham ............................ 210/787 |

FOREIGN PATENT DOCUMENTS

JP          S583658          1/1983

OTHER PUBLICATIONS

IonWorks Barracuda Automated Patch Clamp System User Guide, Feb. 2012, pp. 1-45.
U.S. Appl. No. 13/569,119, filed Aug. 7, 2012, entitled: "Centrifuge Apparatus, Centrifuge Tubes, and Methods for Automated Cell Preparation".
U.S. Appl. No. 13/569,137, filed Aug. 7, 2012, entitled: "Apparatuses and Methods for Conditioning and Reorienting Components of an Electrophysiology Measurement System".
Partial European Search Report from European Patent Application No. 13181634.0, mail date of Jan. 29, 2014.

* cited by examiner

*Primary Examiner* — Sally Merkling
(74) *Attorney, Agent, or Firm* — Bella Fishman

(57) ABSTRACT

A device for separating materials of different densities is provided. A cup body has an internal cavity configured to hold media. An inner wall defines a central body region having an upper and lower end. The upper end is wider than the lower end. An interior shoulder circumscribes the upper end of the central body region. The interior shoulder defines a neck region above the central body region and a shoulder trap below the neck region. The shoulder trap circumscribes the upper end of the central body region and is wider than the neck region. When the device is spun about a central axis, the media travels upward along the inner wall toward the shoulder trap. Relatively more dense material in the media is collected in the shoulder trap, and relatively less dense material is expelled from the device through an opening above the neck region.

6 Claims, 15 Drawing Sheets

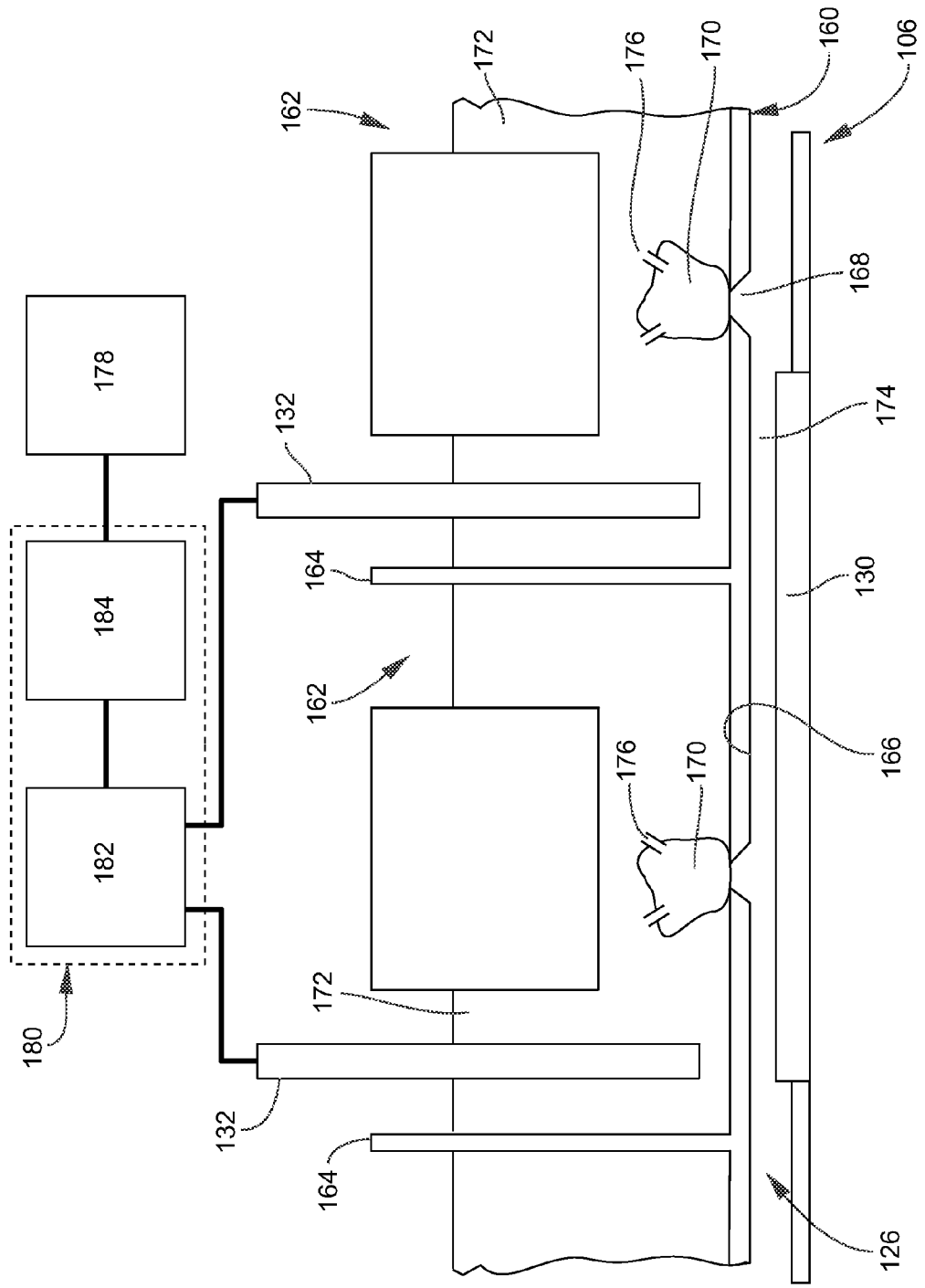

APPARATUS AND METHOD FOR SEPARATING MATERIALS OF DIFFERENT DENSITIES

RELATED APPLICATIONS

This application is related to utility patent applications titled CENTRIFUGE APPARATUS, CENTRIFUGE TUBES, AND METHODS FOR AUTOMATED CELL PREPARATION and APPARATUSES AND METHODS FOR CONDITIONING AND REORIENTING COMPONENTS OF AN ELECTROPHYSIOLOGY MEASUREMENT SYSTEM both filed on Aug. 7, 2012.

TECHNICAL FIELD

This invention relates to automated and semi-automated electrophysiology analysis and in particular relates to high-throughput automated electrophysiology measurement systems.

BACKGROUND

The electrical behavior of cells and cell membranes is of profound importance in basic research as well as in modern drug development. A specific area of interest in this field is in the study of ion channels and transporters. Ion channels are protein-based pores found in the cell membrane that are responsible for maintaining the electrochemical gradients between the extracellular environment and the cell cytoplasm. Ion channels are passive elements in that, once opened, ions flow in the direction of existing electrochemical gradients.

The study of ion channels is a very diverse and prolific area encompassing basic academic research as well as biotechnical and pharmaceutical research. Electrophysiology is performed on isolated cell membranes or vesicles as well as on synthetic membranes where solubilized channels are reconstituted into a manufactured membrane. Instrumentation for automated, high-throughput studies of ion channels have been developed and may be referred to as high-throughput electrophysiological measurement systems.

Generally, many types of assays require adequate cell preparation. Thus, an ongoing need exists for effective methods for cell preparation and apparatuses or devices configured to implement such methods. Adequate cell preparation is of particular interest in the context of automated assays, which may entail performing multiple assays with minimal human intervention to increase throughput and hence the number of data points acquired per day. While known automated high-throughput measurement systems such as noted above may be employed to perform electrophysiological assays in a relatively quick and efficient manner, such systems may not be equipped to automatically prepare the cells and cell solutions used in the assays. Therefore, a need exists for systems and methods to automatically prepare the cells and cell solutions used in electrophysiology assays.

SUMMARY

A device for separating materials of different densities is provided. A cup body has an internal cavity configured to hold media. An inner wall defines a central body region having an upper and lower end. The upper end is wider than the lower end. An interior shoulder circumscribes the upper end of the central body region. The interior shoulder defines a neck region above the central body region and a shoulder trap below the neck region. The shoulder trap circumscribes the upper end of the central body region and is wider than the neck region. When the device is spun about a central axis, the media travels upward along the inner wall toward the shoulder trap. Relatively more dense material in the media is collected in the shoulder trap, and relatively less dense material is expelled from the device through an opening above the neck region.

A method for preparing a cell suspension from a starting mixture that includes relatively less dense buffer solution and relatively more dense cells is also provided. The starting mixture is dispensed into a device having a cup body with an internal cavity to hold the starting mixture. The device is spun about a central axis such that the starting mixture is driven upward along the inner wall of the cup body toward a shoulder trap that circumscribes the internal cavity. The relatively more dense cells in the starting mixture are collected in the shoulder trap, and at least some of the relatively less dense buffer solution in the starting mixture is expelled from the device through an opening of the cup body.

An apparatus for separating materials of different densities is further provided. A separation cup has an internal cavity configured to hold media. The separation cup includes a shoulder trap that circumscribes the internal cavity. The shoulder trap is configured such that, when the separation cup is spun about a central axis, relatively more dense material in the media is collected in the shoulder trap, and relatively less dense material in the media is expelled from the separation cup. A rotary actuator is coupled to the separation cup and is configured to spin the separation cup about a central axis of the separation cup.

BRIEF DESCRIPTION OF THE DRAWINGS

The invention may be better understood by referring to the following figures. The components in the figures are not necessarily to scale, emphasis instead being placed upon illustrating the principles of the invention. In the figures, like reference numerals designate corresponding parts throughout different views.

FIG. 3 is a side cross-sectional view of an example implementation of a patch plate supported on a plenum of an automated high-throughput electrophysiology measurement system.

DETAILED DESCRIPTION

Apparatuses, devices, systems and methods for separating materials of different densities are shown and described. The apparatus may, for example, be utilized for the automated preparation of cells used in biological assays such as electrophysiological assays performed by an automated, high-throughput electrophysiology measurement system. Preparing cells for biological assays may include, for example, ensuring that the cells are suspended in a desired buffer solution, at a desired concentration, and at a desired level of homogeneity. It will be understood, however, that the apparatus may be employed for separating materials of different densities in contexts beyond cell preparation for biological assays.

As disclosed herein, an apparatus (or device, or system) for separating materials of different densities may include a separation cup configured for holding flowable media, which may include materials of different respective densities. The separation cup may include one or more internal features that separate materials of different densities held within the separation cup. Methods for preparing cell solutions are also disclosed, including methods for suspending cells in a desired buffer solution at a desired concentration and at a desired level of homogeneity. In some implementations, the apparatus for separating materials may be utilized in performing one or more of the methods. For example, cells may be prepared by controlling one or more operating parameters of the apparatus such as, for example, the acceleration and deceleration rates of the separation cup, the rotational speed of the separation cup, the spin direction of the separation cup, and the duration of the spin. The apparatus may be provided at the process deck of an automated high-throughput electrophysiology measurement system thereby enabling on-deck automated preparation of cell concentrations. These and other aspects relating to the cell preparation apparatus and methods will be discussed in further detail below.

Figure 1:
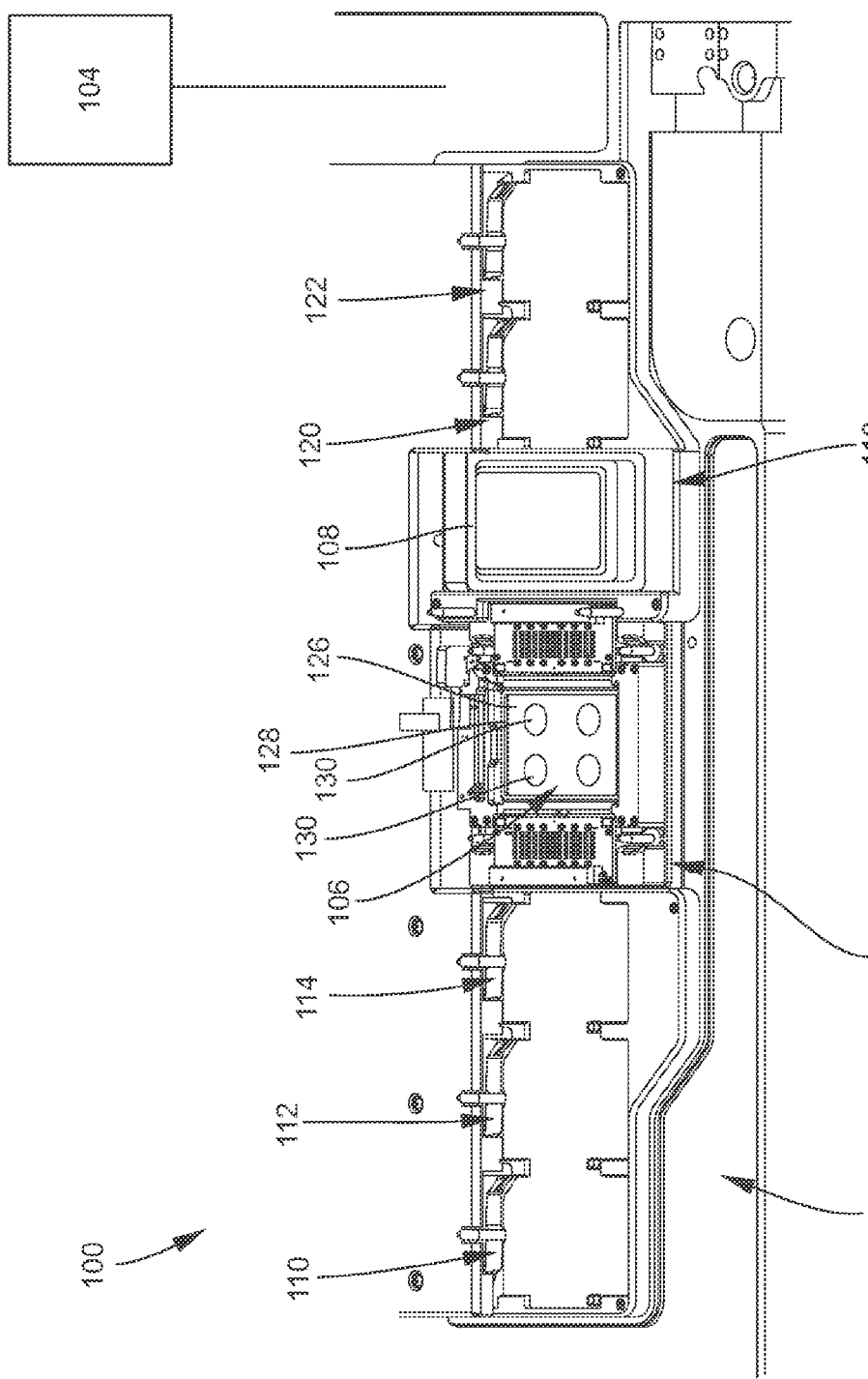
FIG. 1 is a top view of an example of an implementation of an automated high-throughput electrophysiology measurement system.

Referring to FIG. 1, an example of an implementation of an automated high-throughput electrophysiological measurement system 100 is shown in a top view. The system 100, in this example, is configured to conduct simultaneous measurements on multiple samples (e.g., a two-dimensional grid or array of samples). The high-throughput electrophysiological measurement system 100 may include a measurement platform 102, which may also be referred to as a process deck 102. The process deck 102 may support the various components of the system 100 and may comprise a generally planar surface for supporting or maintaining a desired spatial arrangement of some or all of the components of the measurement system 100.

The system may include a control module 104 that controls operation of the system 100 during an assay. The control module 104 may include, for example, an external microcomputer, display device, and software user interface. The control module 104 may also include a microcontroller interfaced to the external microcomputer for controlling the real-time functional aspects of the system 100 including motion control, fluidics control, and electrical data recording.

The system 100 may also include a patch engine that controls the components of the system 100, performs electrophysiological measurements, and digitizes the data acquired during patch clamp assays. The patch engine, in this example, includes a plenum 106, electrode plate 108, and data acquisition engine. These components will be discussed in further detail below.

The system 100 may include multiple stations or modules configured for implementing various functions. In the illustrated example, the system 100 includes seven stations: a tip rack station 110; an external buffer station 112; a first compound station 114; an analysis station 116; a wash station 118; a second compound station 120; and a cell station 122. It will be understood that the system 100 may include more or less stations, including stations providing functions different from those just noted.

Each of the stations, in this example, is shaped to receive an SBS-standard 384-well microtitre plate (Society for Biomolecular Sciences). In other words, the stations, in this example, may be described as having an SBS-standard 384-well microplate footprint. Assay steps take place at the process deck 102, and a robotic pipettor head delivers fluids from the external buffer station 112, cell station 122, and compound stations 114 and 120 to a measurement substrate at the analysis station 116. The robotic pipettor head will be discussed further below with reference to FIG. 2.

The measurement substrate may be referred to as the patch plate and may include multiple holes or apertures around which corresponding samples (e.g., cells or cell membranes) may be positioned or sealed for analysis. The patch plate, in this example, is an SBS-standard 384-well microplate. Accordingly, the patch plate, in this example, includes 384 individual wells for holding cells, external buffer solution, and biological screening compounds. The 384 wells of the patch plate, in this example, may be arranged in a grid of 16 rows (identified as A-P) and 24 columns (identified as 1-24). The wells of the patch plate may include one or more apertures formed through the lower surface. Each aperture may have a diameter of, for example, about 2 micrometers (μm). A patch plate having one aperture per well may be referred to as a single-hole plate. A patch plate having multiple apertures per well (e.g., an array of 64 apertures) may be referred to as a population patch clamp (PPC) plate. The patch plate may be moved to and from the analysis station during an assay. The patch plate will be discussed further below with reference to FIG. 3.

The tip rack station 110 holds a tray that may be preloaded with pipettor tips. The robotic pipettor head may lower onto the tip rack station 110 to load the pipettor tips at the start of an assay. The pipettor tips may be utilized to aspirate and dispense external buffer solution, compounds, and cells at appropriate times during a given assay, depending on the particular method specified for the assay.

The external buffer station 112 may also be referred to as an input station and may include an external buffer boat that holds external buffer solution. In some example implementations, a peristaltic pump and vacuum-assisted waste bottle may be selectively employed to automatically fill and drain the external buffer station 112. The external buffer boat may be filled with external buffer solution prior to the start of an assay. The external buffer solution may be a physiological saline solution comprising a salt or mixture of salts that mimics extracellular solution (e.g., a solution containing low concentrations of potassium). The robotic pipettor head may aspirate the external buffer solution from the external buffer station 112, transport the external buffer solution to the analysis station 116, and dispense the buffer solution into the wells of the patch plate.

The first and second compound stations 114 and 120 may also be referred to as input stations and hold biological screening compounds or other types of reagents that may be utilized during the assay. An SBS-standard 384-well compound plate (e.g., a microplate) may hold the biological screening compounds and reside within the footprint at the first or second compound station 114 or 120. The robotic pipettor head may similarly aspirate the compounds from the compound stations 114 and 120, transport the compounds to the analysis station 116, and dispense the compounds into the wells of the patch plate.

The analysis station 116 includes the plenum 106 of the patch engine and supports the patch plate during the assay. The plenum 106 includes a reservoir 126, and an internal buffer solution may be pumped into and out of the plenum reservoir 126 from below during an assay. The internal buffer solution may be a saline solution comprising a salt or mixture of salts that mimics the internal cytoplasm of a living cell (e.g., a solution containing high concentrations of potassium). The patch plate rests on the plenum 106, and an o-ring 128 surrounding the perimeter of the plenum 106 creates an air-tight seal between the patch plate and the plenum reservoir 126. A small negative (differential) pressure is introduced that pulls cells (or cell membranes) residing in the wells toward the aperture at the bottom of the well. The differential pressure thus forms a high-resistance electrical seal between the cell (or cell membrane) and the bottom of the well, as appreciated by persons skilled in the art.

The electrode plate 108 may be referred to as an electronics head and is used to perform electrophysiological measurements on cell samples at the patch plate. Electrophysiological measurements may be performed by forming an electrical circuit across the apertures in the wells of the patch plate. An electrical circuit may be formed by positioning electrodes on opposite sides of the membrane of the patch plate. For example, a sense electrode may be positioned above the membrane, and a ground electrode may be positioned below the membrane. Accordingly, the plenum 106, in this example, includes four ground electrodes 130 positioned at the top of the plenum reservoir 126, and the electrode plate 108, in this example, may include an array of sense electrodes 132 housed in a frame that fits on top of the patch plate and plenum. The electrode plate 108 will be discussed in further detail below with reference to FIG. 2 and FIG. 3.

The arrangement of the sense electrodes 132 of the electrode plate 108 may correspond to the arrangement of the wells of the patch plate such that each sense electrode 132 may perform an electrophysiological measurement at a respective well of the patch plate. Accordingly, the electrode plate 108, in this example, may include an array of 384 sense electrodes 132. Each sense electrode 132 may correspond to an electronic channel. Accordingly, the 384 sense electrodes 132 in this example correspond to 384 electronic channels.

The electrodes 132 may be, for example, silver or silver-coated pins (i.e., Ag/AgCl). To complete the circuit, a suitable electrolyte (e.g., saline) solution may be added to the wells of the patch plate and the plenum reservoir 126. For example, the external buffer solution and the internal buffer solution may contain chloride ions to enable the sense electrodes 132 and ground electrodes 130 to monitor electrical activity.

The electrode plate 108 may be clamped to the plenum 106 during an assay such that the sense electrodes 132 are received into respective wells of the patch plate. The electrode plate 108 may include apertures formed through its upper surface to provide access to the pipettor tips. In this way, the electrode plate 108 allows for the addition of compounds to the patch plate wells while simultaneously measuring ion current in the wells. As discussed further below with reference to FIG. 3, the sense electrodes 132 and the ground electrodes 130 may be coupled to measurement electronics to obtain data relating to the electrophysiological measurements.

The wash station 118 may receive various components in order to clean those components following an assay. The wash station 118, in this example, includes a reservoir that accommodates the pipettor tips and the electrode pins of the electrode plates for the washing procedures. Accordingly, the wash station 118, in this example, may include a manifold of input ports that match the dimensionality of the pipettor tips and electrode pins. A fluid handling system (not shown) may pump cleaning solution through the wash station 118, which may then empty into waste carboys (not shown) below the process deck 102. The wash station 118 may also serve as a resting position for the electrode plate when not in use. The robotic pipettor head may pick up the electrode plate 108 at the wash station 118 and transport the electrode plate 108 to the analysis station 116 during an assay. The robotic pipettor head may then return the electrode plate 108 to its resting position at the wash station 118 at the conclusion of an assay.

The cell station 122 may also be referred to as an input station and include a cell boat that holds the cells (or other biological samples) used in an assay. The cells may be suspended in an external buffer solution while residing in the cell boat. The robotic pipettor head may similarly aspirate the cells from the cell station 122, transport the cells to the analysis station 116, and dispense the cells into the wells of the patch plate.

Figure 2:
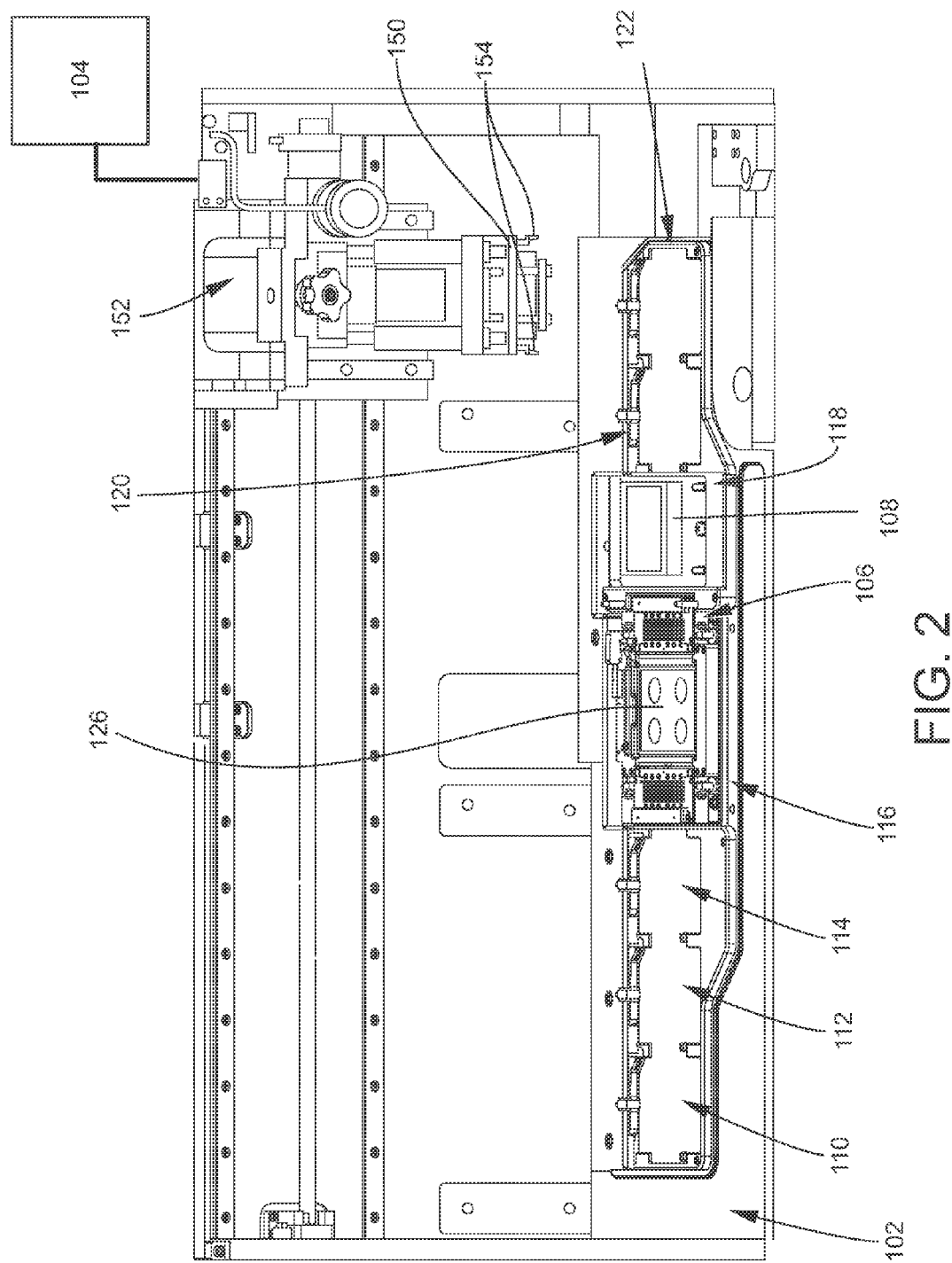
FIG. 2 is a side view of an example of an implementation of a robotic pipettor head of an automated high-throughput electrophysiology measurement system.

Referring now to FIG. 2, an example of an implementation of a robotic pipettor head 150 for a high-throughput electrophysiology measurement system 100 is shown in a side view. The robotic pipettor head 150 may also be referred to as a fluidics head or a multi-channel dispensing head. The robotic pipettor head 150 may be used to add, remove, replace, or transfer fluids, cell solutions, and compounds into the wells of a patch plate. The robotic pipettor head 150, in this example, may hold the pipettor tips utilized to transport fluids from the cell station 122, the external buffer station 112, and the compound stations 114 and 120 to the analysis station 116. The pipettor tips aspirate or dispense the fluids in precise amounts according to the assay protocols.

The robotic pipettor head 150 may be coupled to a three-dimensional mechanical gantry system 152 for moving the robotic pipettor head 150 between the stations of the process deck. The control module 104 may communicate with the mechanical gantry system 152 to control the movement of the robotic pipettor head 150 during an assay.

At the start of an assay, the robotic pipettor head 150 may move to the tip rack station 110 and load the pipettor tips. The robotic pipettor head 150 may also serve as the transport mechanism for the electrode plate 108. Accordingly, the robotic pipettor head 150 may, for example, include electrode plate transport clips 154 that hold the electrode plate 108. The robotic pipettor head 150 may load the electrode plate 108 from its resting position at the wash station 118 and transport it to the analysis station 116 where it clamps to the plenum 106 during the assay. At the conclusion of the assay, the robotic pipettor head 150 may load the electrode plate 108 from the analysis station 116 and transport it back to the wash station 118.

Referring now to FIG. 3, an example implementation of a patch plate 160 supported by a plenum 106 of a high-throughput electrophysiology measurement system 100 is shown. The patch plate 160 may include multiple wells 162 as discussed above (e.g., 384 wells). Two wells 162 of the patch plate 160 are shown by way of example in FIG. 3. Each well 162 is partitioned by a well wall 164 and bounded by the bottom of the patch plate 160. Additionally, the wells 162 in the example patch plate 160 of FIG. 3 each include an aperture 168 formed through the bottom of the patch plate 160. Cells 170 in the respective wells 162 may be sealed to the bottom of the patch plate 160 via differential pressure as discussed above.

The wells 162 of the patch plate 160 may be filled with external buffer solution 172, and the plenum reservoir 126 of the plenum 106 situated beneath the patch plate 160 may be filled with internal buffer solution 174. Sense electrodes 132 may be positioned in the respective wells 162 of the patch plate 160 to measure the electrical activity occurring in the wells 162 during the assay, such as the activity of ion channels 176 of the cells 170 as appreciated by persons skilled in the art. The ground electrodes 130 of the plenum 106 may complete the electrical circuits across the respective apertures 168 of the patch plate 160.

The sense electrodes 132 of the electrode plate 108 and the ground electrodes 130 may communicate with the data acquisition engine 178 via measurement electronics 180 such as, for example, a programmable voltage source (not shown), an amplifier 182 and analog-to-digital converter (ADC) 184. As seen in the example shown in FIG. 3, the sense electrodes 132 and the ground electrodes 130 are in signal communication with the amplifier 182, which is in signal communication with the ADC 184, which is in turn in signal communication with the data acquisition engine 178. The amplifier 182 may be a high-gain, low-noise trans-impedance amplifier that converts the current measured on the sense electrode 132 to an analog voltage signal. The ADC 184 may convert the analog voltage signal from the amplifier 182 into a digital voltage measurement. The data acquisition engine 178 may thus save the digital voltage measurements for the sense electrode channels in a computer memory.

Figure 4A:
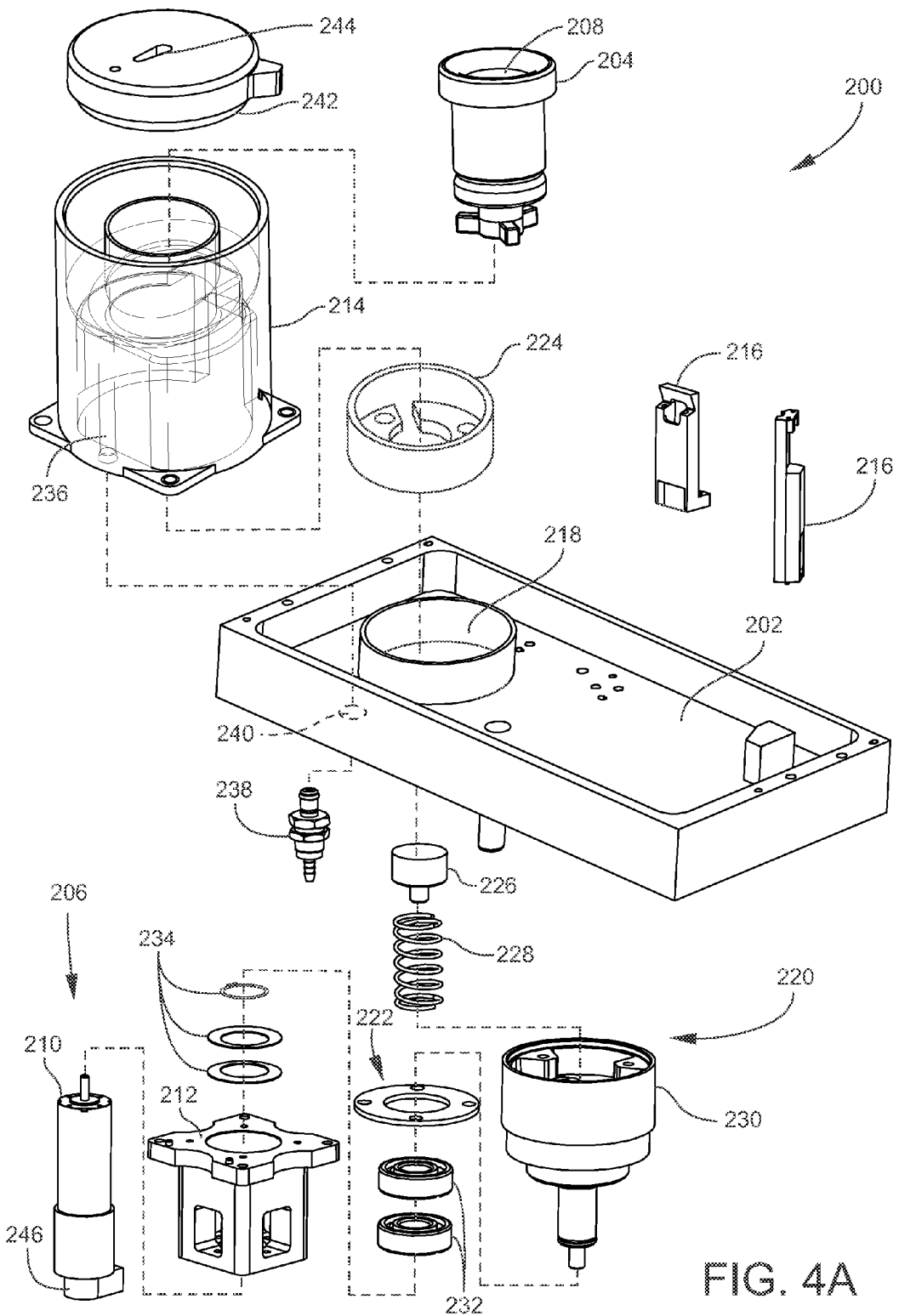
FIG. 4A is an exploded view of an example of an implementation of an apparatus for separating materials of different densities.

Referring now to FIG. 4A, an exploded view of an example of an implementation of an apparatus 200 for separating materials of different densities is shown. A mounting frame 202 supports a separation cup 204 and a rotary actuator 206. The rotary actuator 206 drives rotation of the separation cup 204 about a central axis to separate materials of different densities. The mounting frame 202 may be, for example, part of a process deck 102 of an automated high-throughput electrophysiology measurement system 100 such as illustrated in FIGS. 1 and 2. As discussed further below, the separation cup 204 includes internal features that trap relatively high-density material while allowing relatively low-density material to exit the cup 204 through an opening 208 at the top of the cup 204.

The rotary actuator 206 includes a motor 210 and is mounted to the underside of the mounting frame 202 by an actuator housing 212. The separation cup 204 is received and positioned in a cup housing 214. The cup housing 214 is mounted to the top side of the mounting frame 202 and may be secured to a pair of support frames 216 that also mount to the top side of the mounting frame 202.

As discussed further below, the separation cup 204 is coupled to the rotary actuator 206 through an opening 218 formed through the mounting frame 202 via a cup mounting assembly 220 and a rotor assembly 222. The cup mounting assembly 220, in this example, includes a cup mount 224, a support pad 226, a biasing spring 228, and a rotary actuator mount 230. The rotor assembly 222, in this example, includes a pair of ball bearings 232 that facilitate the rotation of the cup mounting assembly 220. The rotor assembly 222 may also include one or more washers 234, which may be used to selectively adapt different types of motors to the actuator housing 212.

As seen in FIG. 4A, the cup housing 214, in this example, includes a drainage tube 236 that may fluidly communicate with a drainage nozzle 238 through a drain opening 240 formed through the mounting frame 202. The drainage nozzle 238 may be connected to a plumbing system (not shown) in order to transport away the relatively low-density material spun out of the separation cup 204. As also seen in FIG. 4A, a housing cap 242 may cover the top side of the cup housing 214 in order to enclose the separation cup 204 when the separation cup 204 is situated in the cup housing 214. An opening 244 is formed through the housing cap 242, in this example, to permit a pipettor to access the interior of the cup housing 214. The opening 244 in the housing cap 242, in this example, is positioned above the separation cup 204 so that the pipettor may aspirate material from or dispense material into the separation cup 204.

Figure 4B:
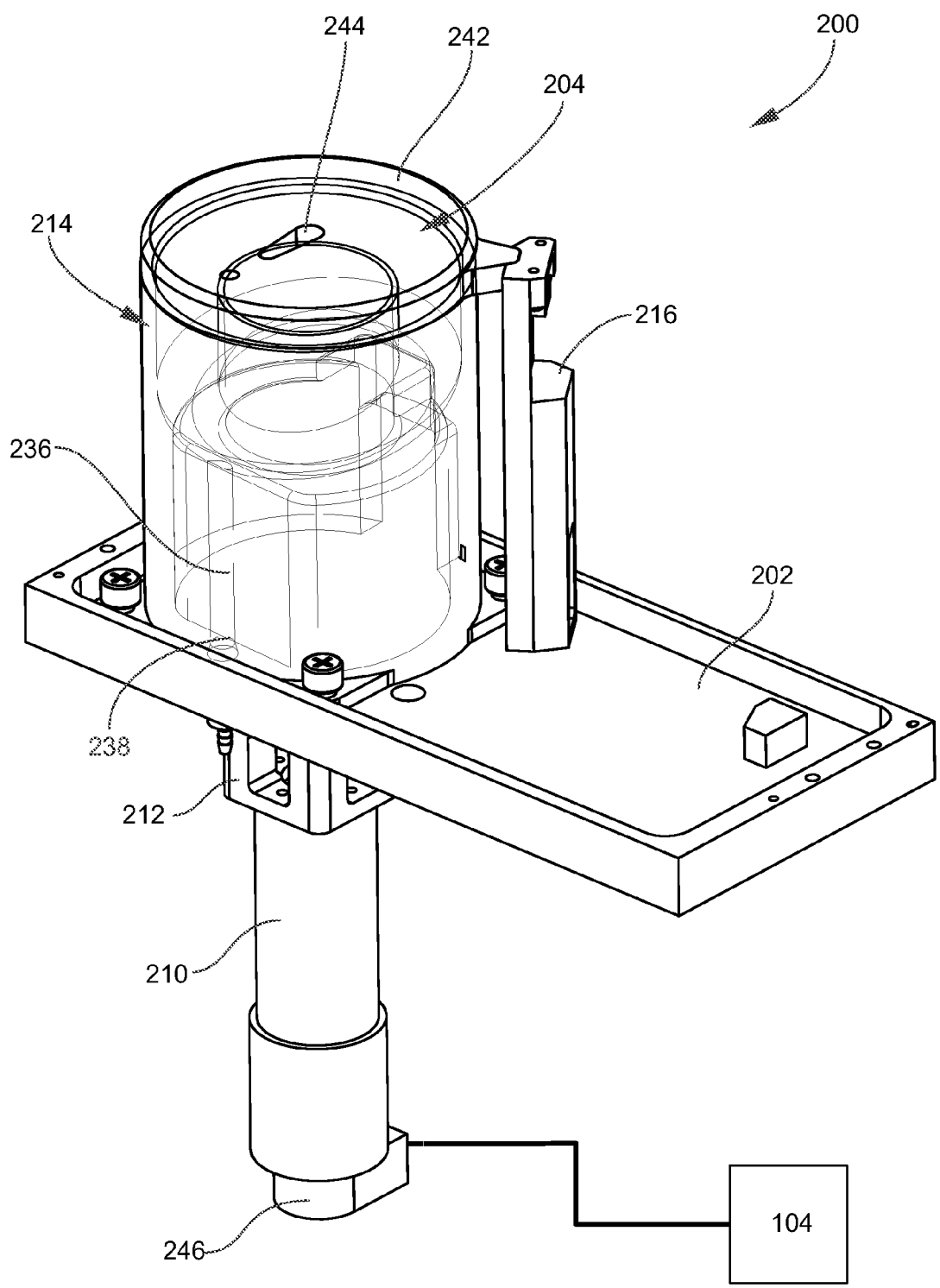
FIG. 4B is a front top-right perspective view of the automated apparatus for separating materials of different densities of FIG. 4A shown in an assembled configuration.

FIG. 4B is a front top-right perspective view of the apparatus 200 for separating materials of different densities of FIG. 4A shown in an assembled view. As seen in FIG. 4B, the separation cup 204 is situated in the cup housing 214, which is mounted to the mounting frame 202. The separation cup 204 is coupled to the rotary actuator 206 through the opening 218 formed through the mounting frame 202. Accordingly, the rotary actuator 206 may drive rotation of the separation cup 204 to expel relatively low-density material out of the separation cup 204. As discussed further below, the relatively low-density material spun out of the separation cup 204 may drain into the drainage tube 236 and be transported away by a plumbing system (not shown) via the drainage nozzle 238.

The motor 210 may be a brushless direct current (DC) motor coupled to a corresponding encoder 246. The motor 210 may rotate the mounting assembly 220 and the separation cup 204 secured in the mounting assembly 220 about a central axis. The motor 210 of the rotary actuator 206 may communicate with a controller (e.g., a servo drive controller) that controls operation of the motor 210 to rotate the mounting assembly 220 and separation cup 204. The controller, in this example, may be in signal communication with and driven by the control module 104 discussed above with reference to FIG. 1. In this way, the control module 104 may control one or more operating parameters such as rotational acceleration and deceleration, rotational speed, and the duration of rotation of the separation cup 204. The control module 104, in this example, may be the control module discussed above with reference to FIG. 1.

Figure 5:
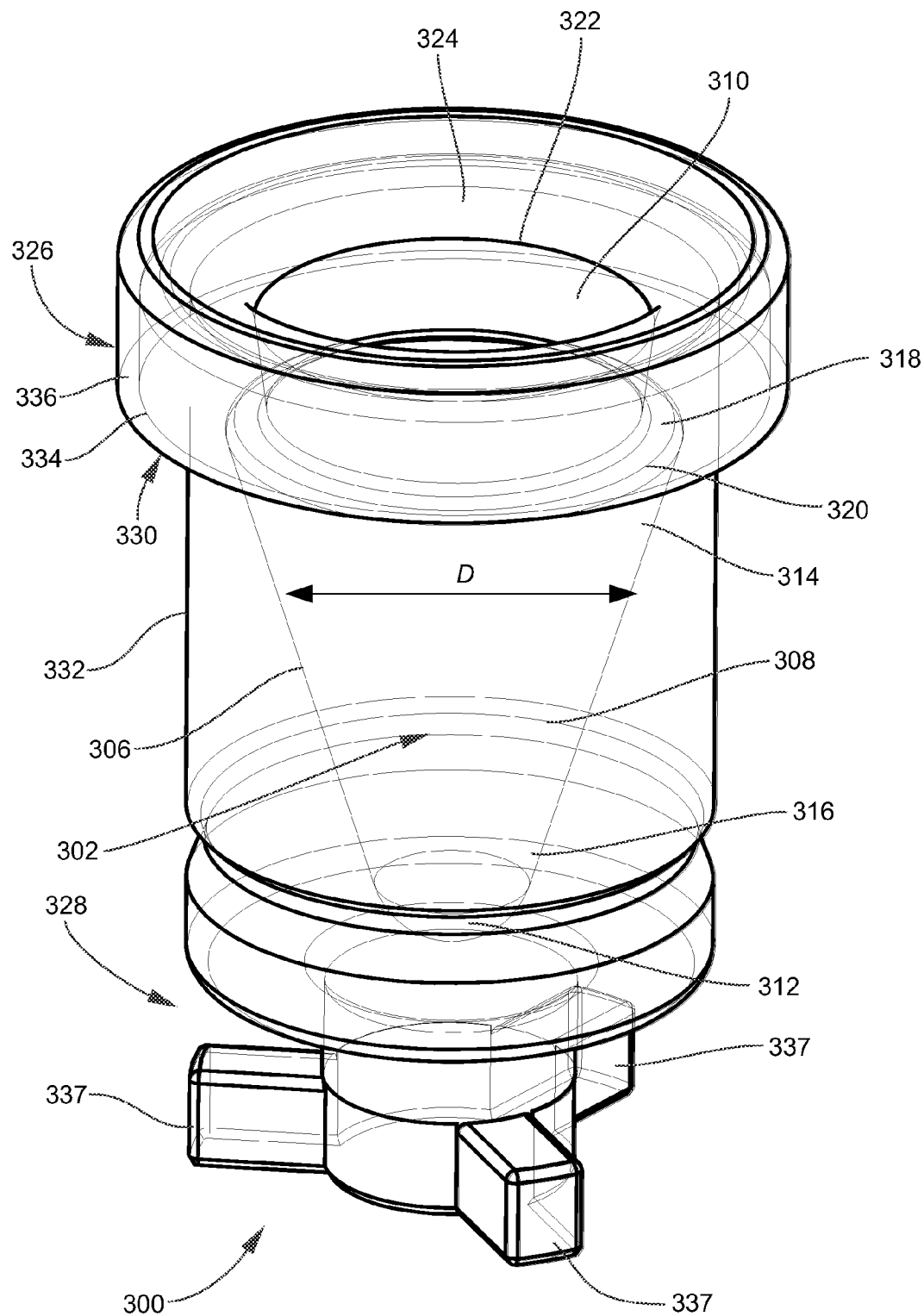
FIG. 5 is a top perspective view of an example of an implementation of a separation cup.
Figure 6:
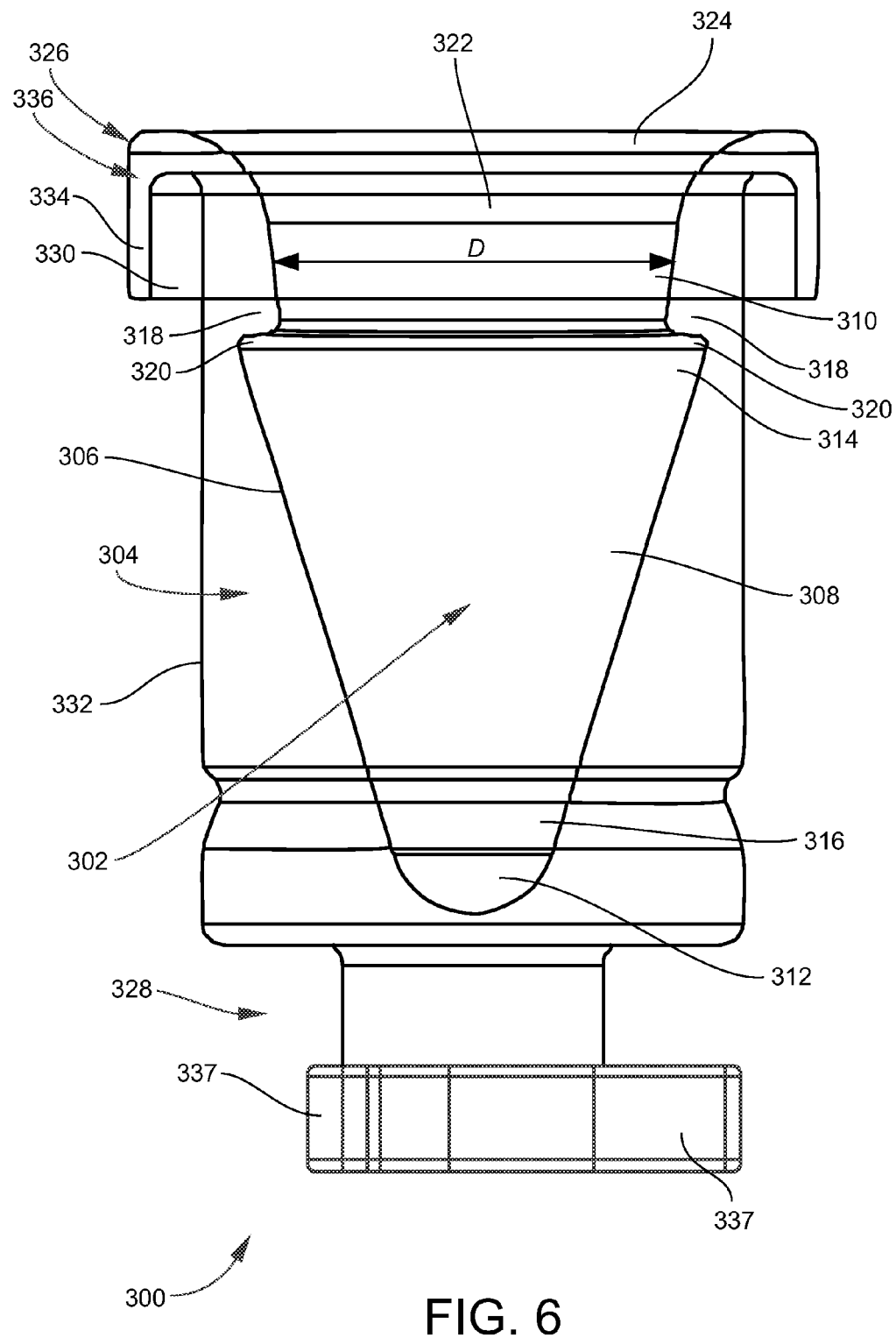
FIG. 6 is a side cross-sectional view of the separation cup of FIG. 5.

Referring now to FIGS. 5 and 6, a top perspective view and side cross-sectional view of an example of an implementation of a separation cup 300 are respectively shown. The separation cup 300 includes an internal cavity 302 formed in a body 304 (FIG. 6) of the separation cup 300. The internal cavity 302 of the separation cup body 304 may hold flowable media such as a solution, suspension, slurry, emulsion, etc. The internal cavity 302 may, for example, hold a starting mixture having the relatively more and relatively less dense materials to be separated. The starting mixture may be, for example, a cell suspension that includes cells suspended in media (e.g., serum, buffer, antibiotics, etc.). Accordingly, an inner wall 306 of the separation cup 300 that at least in part defines the internal cavity 302 may further define various regions of the separation cup 300 including a central body region 308, a neck region 310, and a bottom region 312 as shown by way of example in FIG. 5. The neck region 310 of the separation cup 300, in this example, is situated above the central body region 308, and the bottom region 312 of the separation cup, in this example, is situated below the central body region 308.

The contour of the inner wall 306 facilitates movement of the cell suspension upward along the inner wall 306. In this regard, the internal cavity 302 may have a substantially conical shape as shown by way of example in FIG. 5. In particular, the central body region 308 of the separation cup 300, in this example, may have a substantially frustoconical shape, and the bottom region 312 of the separation cup 300, in this example, may have a substantially hemispherical shape. Accordingly, the upper end 314 of the central body region 308 may be wider than the lower end 316 of the central body region 308, and the diameter, D, of the internal cavity 302 may taper through the central body region 308 downward towards the lower end 316 of the central body region 308. That is, the diameter, D, at the central body region 308 reduces in the direction toward the lower end 316.

The separation cup 300, in this example, also includes a shoulder 318 circumscribing the upper end 314 of the central body region 308. As seen in FIG. 5, the shoulder 318, in this example, defines the neck region 310 above the central body region 308 and a shoulder trap 320 below the neck region 310. The shoulder trap 320 also circumscribes the upper end 314 of the central body region 308 of the separation cup 300. Accordingly, the shoulder 318 and shoulder trap 320 may each be described as having an annular shape. As seen in FIG. 5, the shoulder trap 320 is wider than the neck region 310. In this way, the shoulder trap 320 of the separation cup 300 collects (i.e., traps, localizes, etc.) the relatively more dense materials when the separation cup 300 is spun about a central axis. As the separation cup 300 is spun about a central axis, the cell suspension travels upward along the inner wall 306 toward the shoulder trap 320. The shoulder trap 320 collects the relatively more dense material in the cell suspension while the relatively less dense material in the cell suspension continues to travel upward through the neck region 310 and is expelled from the separation cup 300 through an opening 322 above the neck region 310. The separation cup 300 may also include an opening portion 324 above the neck region 310 that circumscribes the neck region 310. The opening portion 324 may have an outwardly-flared shape, which also facilitates movement of the relatively less dense material up along the inner wall 306 and out from the top as the separation cup 300 spins about a central axis.

The separation cup 300, in this example, also includes a rim 326 surrounding the opening portion 324 of the cup 300, and a base 328 at the bottom of the cup 300. As seen in FIG. 5, an annular notch 330 may be formed in the underside of the rim 326 such that the notch 330 separates the outer wall 332 of the separation cup body 304 from an inward-facing surface 334 of the rim wall 336. The base 328 of the separation cup 300 may include one or more coupling members configured for coupling the separation cup 300 to, and thus being driven by, a rotary actuator such that the separation cup 300 rotates about its central axis. In the illustrated example, the base 328 includes multiple feet 337, which may be used when securing the separation cup 300 within the mounting assembly (220 in FIG. 4A) as discussed further below.

Referring particularly to FIG. 6, as mentioned above the internal cavity 302, in this example, includes from top to bottom a neck region 310, a shoulder trap 320, a central body region 308, and a bottom region 312. In this example, the neck region 310 may be described as having a frustoconical shape, the shoulder trap 320 may be described as having an annular shape, the central body region 308 may also be described as having a frustoconical shape, and the bottom region 312 may be described as having a hemispherical shape. Accordingly, from top to bottom, the inner diameter, D, of the internal cavity 302, in this example, may reduce through the neck region 310, increase through the shoulder trap 320, and reduce through the central body region 308 and the bottom region 312. In this way, the neck region 310, the central body region 308, and the bottom region 312, in this example, may be described as tapering in a downward direction. The shoulder trap 320, in this example, may thus be described as flaring laterally toward the outer wall 332 of the cup body 304. As seen in FIG. 6, the contour of the inner wall 306 may follow a somewhat S-shaped curve through the shoulder trap 320.

As the separation cup 300 is spun about a central axis, centrifugal forces act on the cell suspension held in the cup 300. As the separation cup 300 spins, the centrifugal forces draw the cell suspension toward the tapered inner wall 306. Due to the conical shape of the internal cavity 302, the cell suspension travels up the inner wall 306 toward the annular shoulder trap 320. When the cell suspension reaches the shoulder trap 320, the relatively more dense material in the cell suspension collects in the shoulder trap 320. The relatively less dense material in the cell suspension continues traveling upward past the shoulder trap 320, along the neck region 310, and along the outwardly flared opening portion 324 to exit the separation cup 300.

Also seen in FIG. 6, the rim 326 of the separation cup 300, in this example, is an annular rim 326 that folds back on itself forming an annular notch 330 between the inward-facing surface 334 rim wall 336 of the rim 326 and the outer wall 332 of the body 304 of the separation cup 300. As shown by way of example in FIG. 6, the rim wall 336 of the rim 326 is substantially parallel with the outer wall 332 of the separation cup body 304 with the notch 330 positioned between the rim wall 336 and the outer wall 332.

The separation cup 300 may have a height of around, for example, 100 millimeters (mm), and an outer diameter of around, for example, 70 mm. The internal cavity 302 may have a depth of around, for example, 70 mm, and the inner diameter, D, of the conical internal cavity 302 may taper between, for example, around 35 mm near the upper end 314 of the central body region 308 to around 10 mm near the lower end 316 of the central body region 308.

Figure 7:
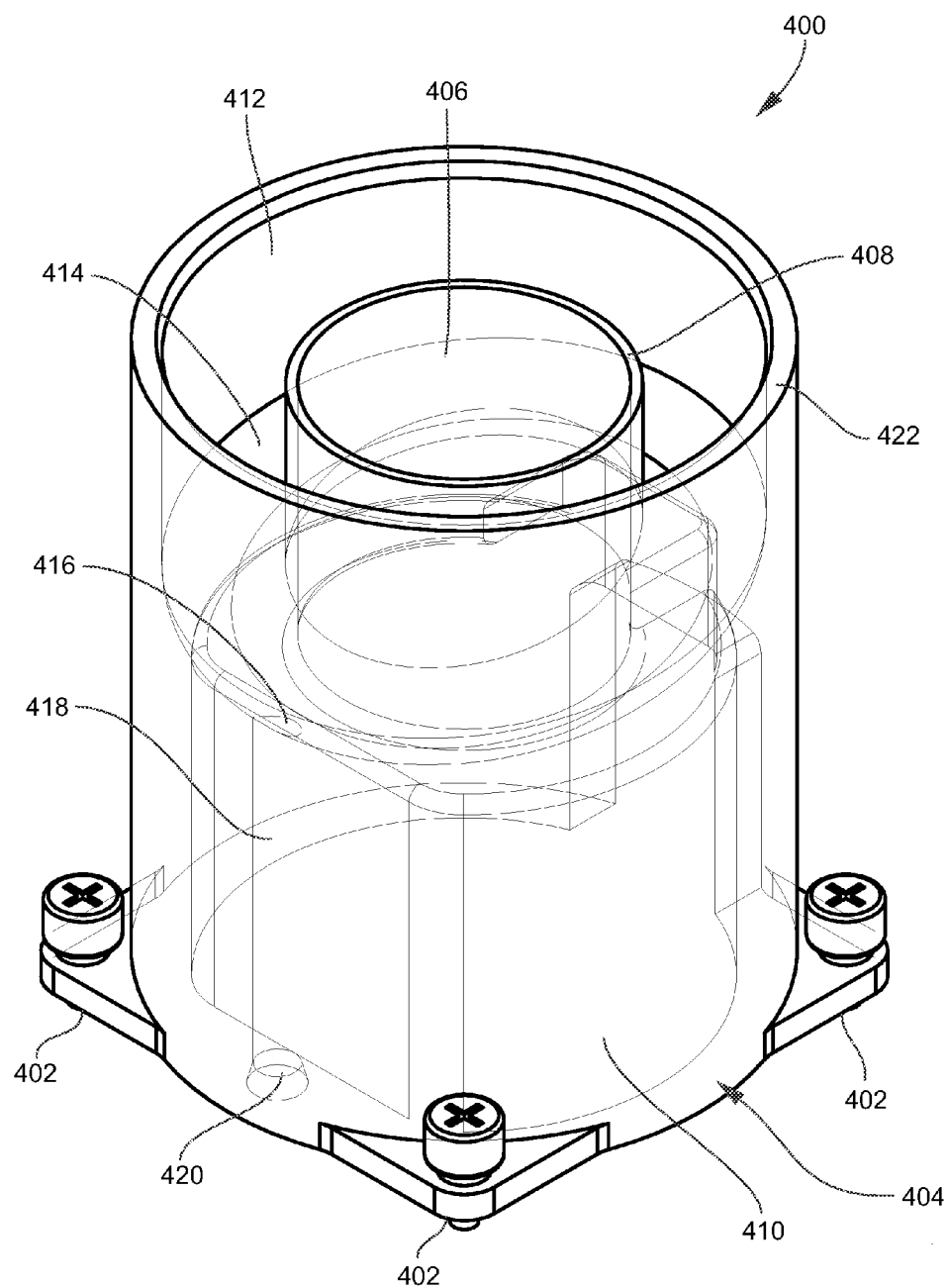
FIG. 7 is a top perspective view of an example of an implementation of a cup housing.

With reference to FIG. 7, a top perspective view of an example of an implementation of a separation cup housing 400 is shown. The separation cup housing 400 may include multiple mounting flanges 402 around the base 404 used to mount the separation cup housing 404 to the mounting frame (202 in FIG. 4A). As discussed above, the separation cup (204 in FIG. 4A) resides within the separation cup housing 400. Accordingly, the cup housing 400 in this example includes a central duct 406 defined by a vertical duct wall 408 and leads to a lower internal chamber 410. The duct wall 408, in this example, has a cylindrical shape.

The separation cup 204 may be inserted through the central duct 406 such that the lower portion of the separation cup 204 (e.g., the base 328 in FIG. 6) resides in the lower internal chamber 410 of the cup housing 400. The underside of the separation cup housing 400, in this example, is open such that the cup mounting assembly (220 in FIG. 4A) may be received and situated in the lower internal chamber 410. The cup housing 400 also includes an annular collection chamber 412 surrounding the central duct 406 and the separation cup 204.

The collection chamber 412 receives the relatively low-density material spun out of the separation cup 202 when the cup 202 is spun in the central duct 406 about a central axis. The floor 414 of the collection chamber 412 is slanted toward an upper drainage opening 416 formed in the floor 414 of the collection chamber 412. A drainage tube 418 connects the upper drainage opening 416 to a lower drainage opening 420 down at the base 404 of the cup housing 400. The lower draining opening 420 may be positioned over a drain opening (240 in FIG. 4A) in the mounting frame 202 that receives a drainage nozzle (238 in FIG. 4A) as mentioned above. In this way, the cup housing 400 facilitates removal of the low-density material spun out of the separation cup 204.

Figure 8:
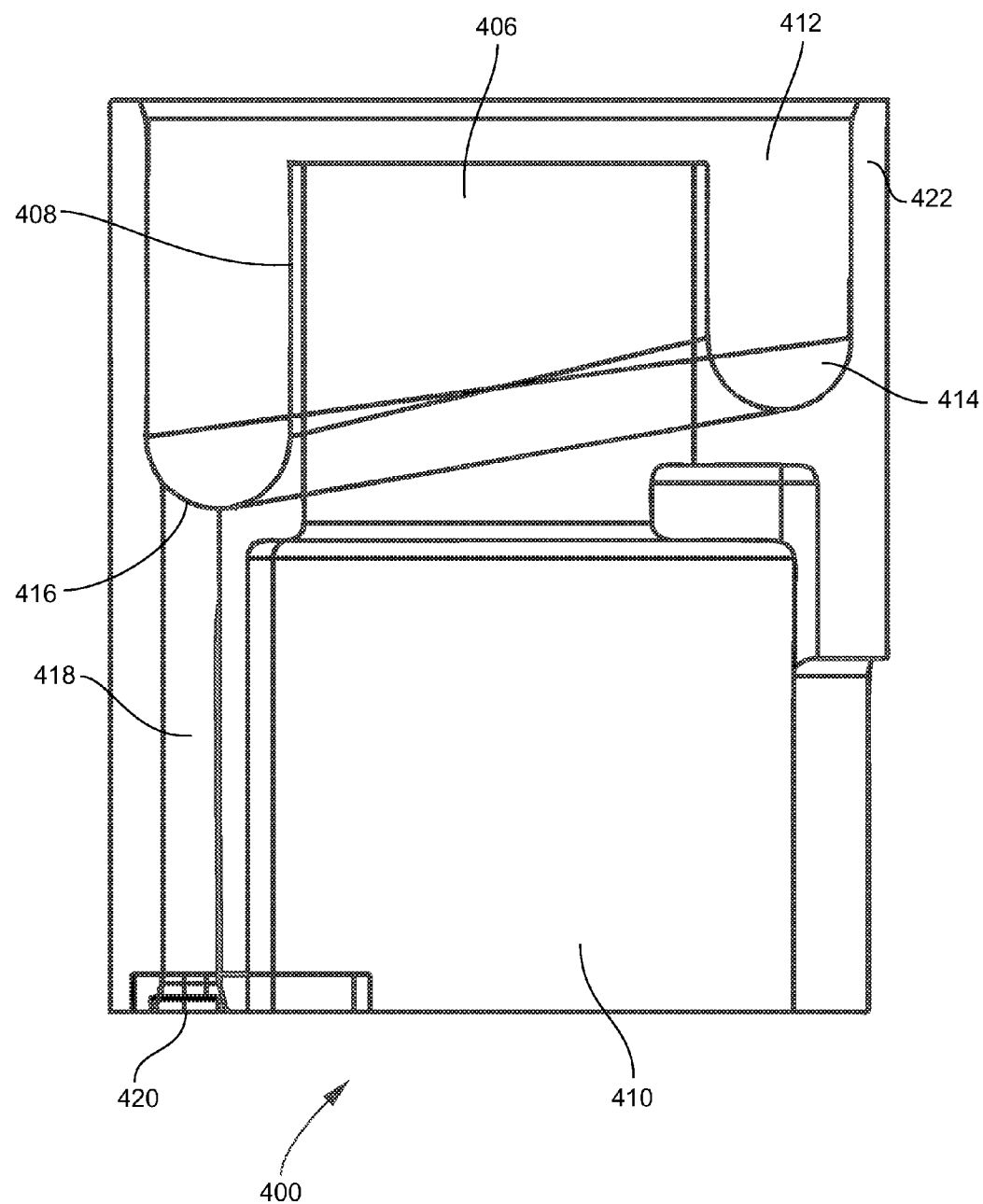
FIG. 8 is a side cross-sectional view of the cup housing of FIG. 7.

FIG. 8 is a side cross-sectional view of the cup housing 400 of FIG. 7. As seen in FIG. 8, the cup housing 400 includes an annular collection chamber 412 formed between the duct wall 408 of the central duct 406 and the outer wall 422 of the cup housing 400. The central duct 406 leads to a lower internal chamber 410 that houses the cup mounting assembly 220 as discussed further below. The floor 414 of the collection chamber 412 slants towards an upper draining opening 416 and drainage tube 418.

Figure 9:
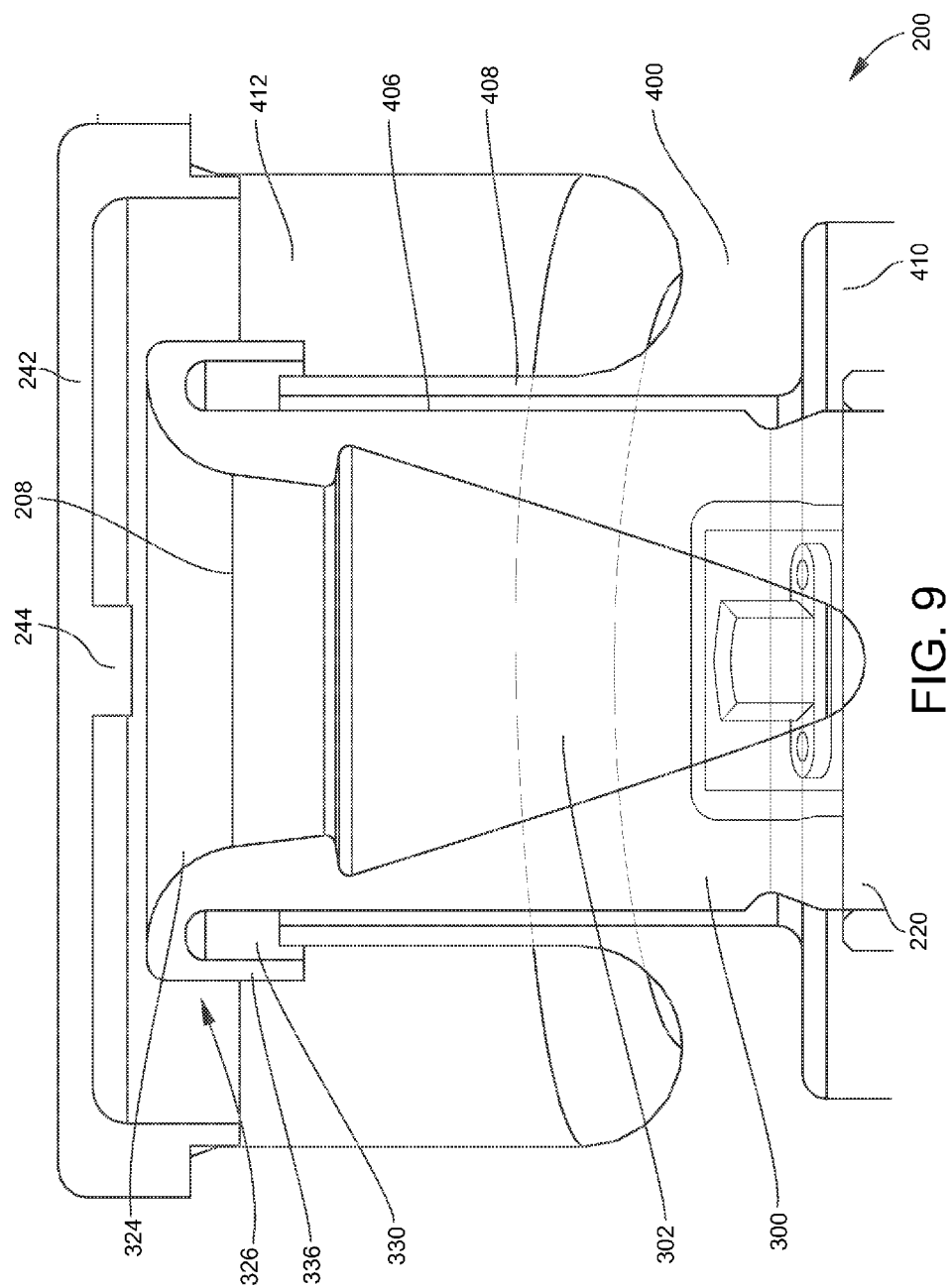
FIG. 9 is a side cross-sectional view of an upper portion of the automated apparatus for separating materials of different densities of FIG. 4A shown in an assembled configuration.

Referring now to FIG. 9, a side cross-sectional view of an upper portion of the apparatus 200 for separating materials of different densities of FIG. 4A is shown in an assembled configuration. As seen in FIG. 9, the separation cup 300 resides within the central duct 406 of the cup housing 400. The duct wall 408 of the central duct 406 separates the separation cup 300 from the collection chamber 412 of the cup housing 400. The separation cup 300 passes through the central duct 406 of the cup housing 400 such that the lower portion of the separation cup 300 resides in the lower internal chamber 410 of the cup housing 400 with the cup mounting assembly 220. The lower internal chamber 410 of the cup housing 400 will be discussed in further detail below with reference to FIG. 11.

Additionally, the top of the duct wall 408 is received in the notch 330 of the rim 326 surrounding the top of the separation cup 300 such that the rim wall 334 of the rim 326 and the duct wall 408 of the central duct 406 overlap as shown by way of example in FIG. 9. In this way, the notch 330 prevents fluid expelled from the separation cup 300 from contacting the outer wall 332 of the separation cup 300. Moreover, the housing cap 242 may cover the top of the cup housing 400 in order to enclose the separation cup 300 residing within the housing 400. The pipettor opening 244 of the housing cap 242 is positioned over the opening 208 of the separation cup 204. In this way, a pipettor may be inserted through the opening 244 of the housing cap 242 in order to aspirate media from and dispense media into the separation cup 300. As seen in FIG. 9, this configuration enables a pipettor to aspirate and dispense media even when the separation cup 300 is spinning.

The configuration of the separation cup 300 and cup housing 400 shown by way of example in FIG. 9 facilitates the separation of relatively high-density and low-density materials using centrifugal forces. As explained above, the separation cup 300 may be spun about a central axis as the cup 300 resides in the cup housing 400. Relatively high-density material is trapped in the shoulder trap 320 of the internal cavity 302, and relatively low-density material exits through the outwardly flared opening portion 324 of the cup 300. The annular collection chamber 412 of the cup housing 400 surrounding the separation cup 300 thus receives the relatively low-density material spun out of the separation cup 300.

Figure 10:
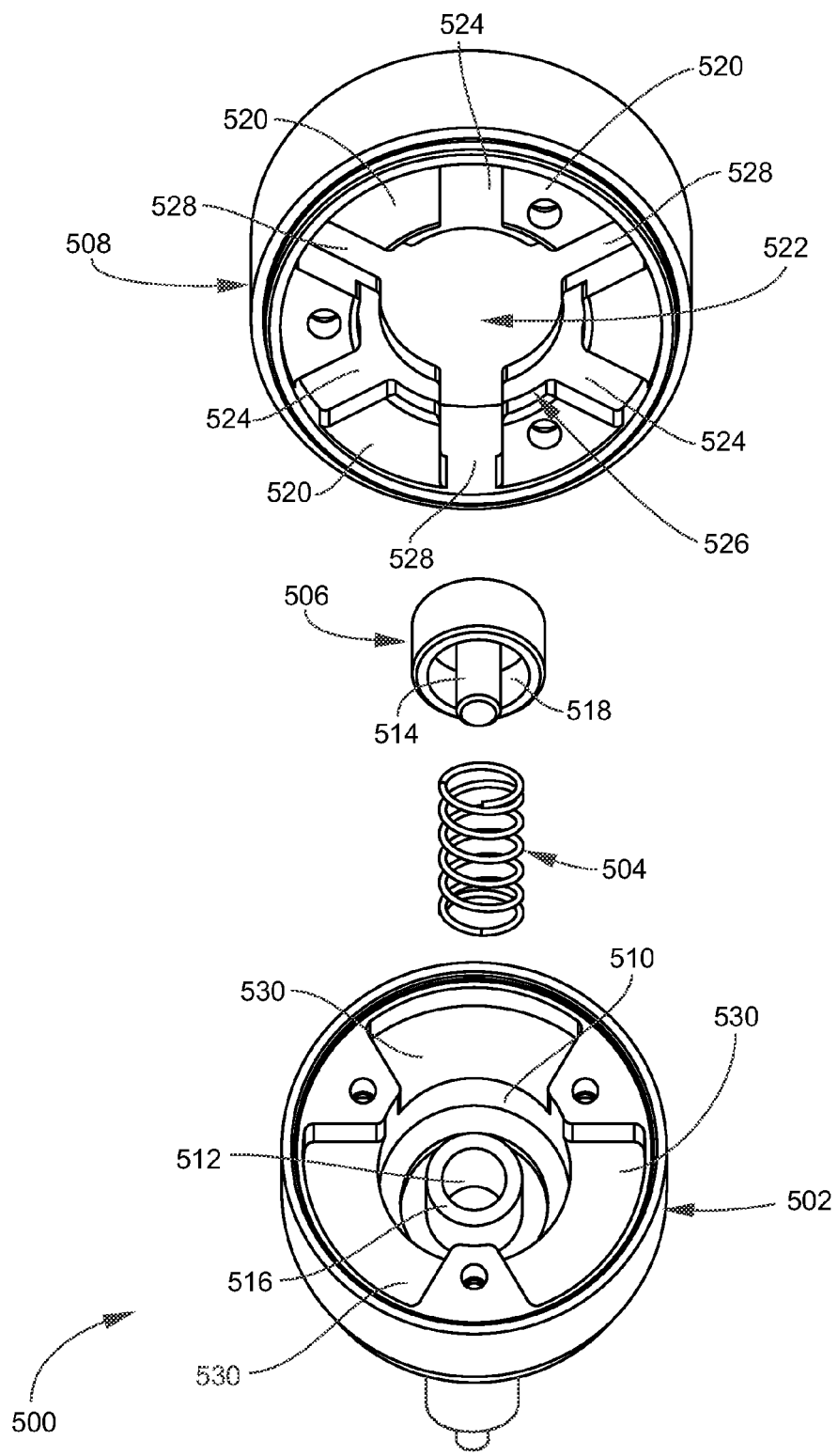
FIG. 10 is a perspective view of an example of an implementation of a cup mounting assembly.

Referring now to FIG. 10, a perspective view of an example of an implementation of a cup mounting assembly 500 is shown. The cup mounting assembly 500, in this example, includes a rotor mount 502, biasing spring 504, support pad 506, and cup mount 508. In this example, the biasing spring 504 and support pad 506 are received in the rotor mount 502, and the cup mount 508 is secured to the rotor mount 502 (e.g., via screws or other attachment means). In FIG. 10, the top side of the rotor mount 502 is shown, and the respective undersides of the support pad 506 and the cup mount 508 are shown.

The rotor mount 502, in this example, includes a recess 510 that receives the biasing spring 504 and support pad 506 as well as a central duct 512 for receipt of a shaft 514 on the support pad 506. The biasing spring 504, in this example, is positioned to surround the walls 516 of the central duct 512 of the rotor mount 502. The biasing spring 504, in this example, is also positioned to surround the shaft 514 of the support pad 506. The support pad 506 also includes a recess 518 formed on its underside for receipt of the biasing spring 504. In this configuration, the biasing spring 504 biases the support pad 506 away from the rotor mount 502. When the biasing spring 504 is loaded, the central duct 512 of the rotor mount 502 receives the shaft 514 of the support pad 506. The rotor mount 502 is coupled to the rotor assembly (222 in FIG. 4A) to receive the rotational force provided by the rotary actuator (206 in FIG. 4A).

The separation cup mount 508, in this example, secures the separation cup (300 in FIG. 5) when the separation cup 300 is situated in the cup housing (400 in FIG. 7). As seen in FIG. 10, the separation cup mount 508 includes a set of internal flanges 520 that define an opening 522 for the base (328 in FIG. 5) of the separation cup 300 formed through the cup mount 508. The base opening 522 defined by the internal flanges 520 has a shape that matches the base 328 of the separation cup 300. Accordingly, the base opening 522 of the cup mount 508 includes respective openings 524 to receive the feet (337 in FIG. 5) on the base 328 of the separation cup 300. The cup mount 508, in this example, also includes a recess 526 for the base 328 of the separation cup 300 formed on the underside of the internal flanges 520. The shape of the base recess 526 on the underside of the internal flanges 520, in this example, also matches the shape the base 328 of the separation cup 300. Accordingly, each internal flange 520, in this example, respectively includes a recess 528 to receive one of the feet 337 on the base 328 of the separation cup 300.

The shape of the base recess 526 on the underside of the cup mount 508, however, is rotated relative to the shape of the base opening 522 of the cup mount 508. Accordingly, the base 328 of the separation cup 300 may be inserted through the opening 522 of the cup mount 508 and rotated such that the feet 337 on the base 328 of the separation cup 300 line up with and are received into the foot recesses 528 formed on the underside of the internal flanges 520. The recesses 528 formed on the underside of the internal flanges 520 may thus secure and lock the feet 337 on the base 328 of the separation cup 300. In this way, the cup mount 508 may apply the rotational force provided by the rotary actuator 206 to the separation cup 300 in order to spin the cup 300 about a central axis.

The rotor mount 502 may also include respective recesses 530 for receipt of the feet 337 on the base 328 of the separation cup 300. As seen in FIG. 10, the foot recesses 530 at the rotor mount 502 are sized and shaped to permit the feet 337 on the base 328 of the to rotate clockwise and counterclockwise in order to respectively line up with the foot openings 524 or the foot recesses 528 of the cup mount 508. In this way, the separation cup 300 may be rotated in one direction to secure the cup 300 to the cup mount 508 by lining up the feet 337 on the base 328 of the cup 300 with the foot recesses 528 formed on the underside of the internal flanges 520. Likewise, the separation cup 300 may be rotated in the opposite direction to remove the cup 300 from the cup mount 508 by lining up the feet 337 on the base 328 of the cup 300 with the foot openings 524 defined by the internal flanges 520. The rotary actuator (206 in FIG. 4A) may include a brake to prevent rotation of the rotary actuator when securing or removing the separation cup 300 in the cup mounting assembly 500.

Figure 11:
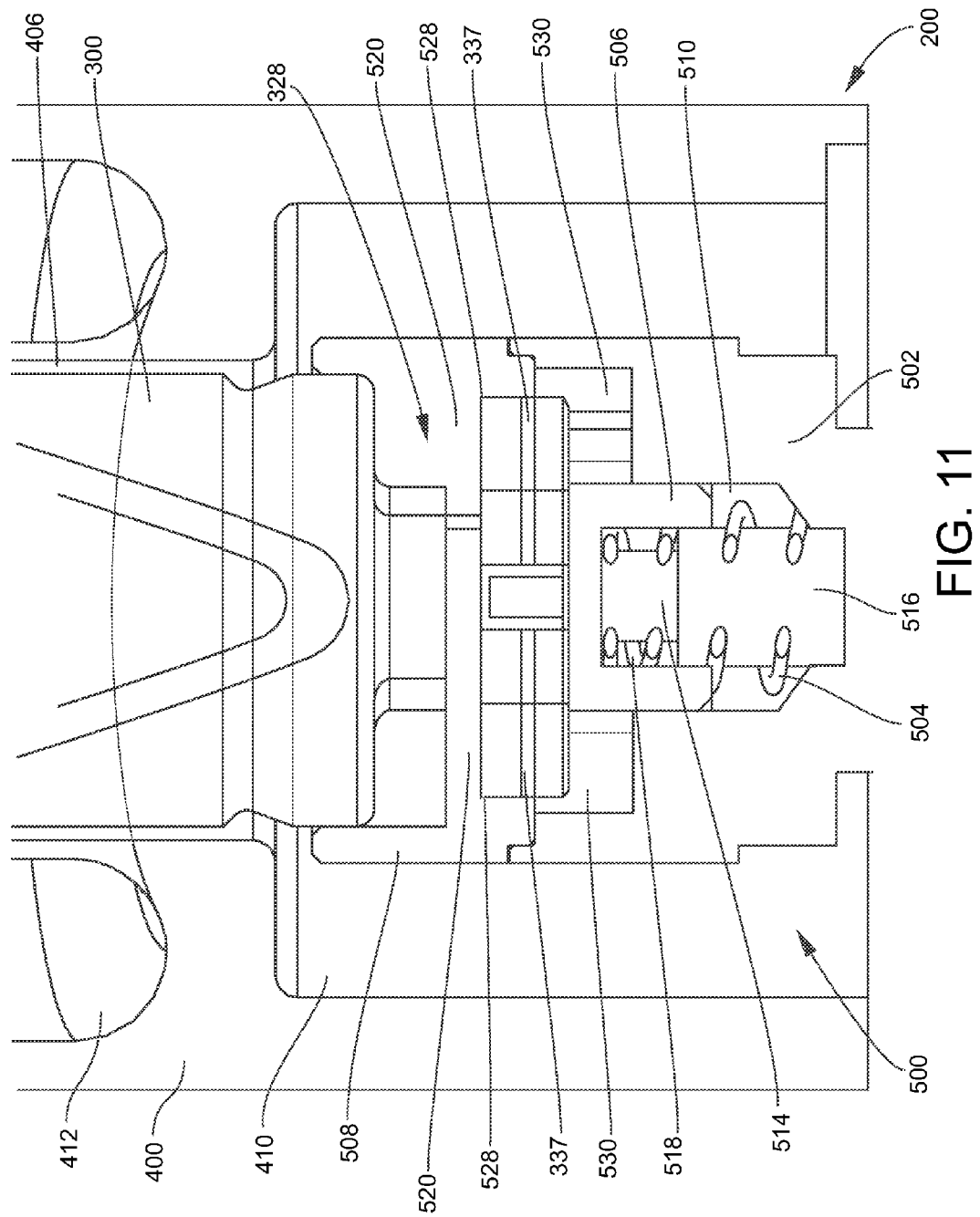
FIG. 11 is a side cross-sectional view of a lower portion of the automated apparatus for separating materials of different densities of FIG. 4A shown in an assembled configuration.

Referring to FIG. 11, a side cross-sectional view of a lower portion of the apparatus 200 for separating materials of different densities of FIG. 4A is shown in an assembled configuration. As seen in FIG. 11, the lower portion of the separation cup 300 and the cup mounting assembly 500 reside in the lower internal chamber 410 of the separation cup housing 400.

When a separation cup 300 is inserted into the separation housing 400, the cup 300 passes through the central duct 406 until the base 328 of the cup 300 engages the cup mounting assembly 500. The separation cup 300 may be rotated until the feet 337 on the base 328 of the cup 300 line up with the foot openings (524 in FIG. 10) of the cup mount 508. With the feet 337 on the base 328 of the separation cup 300 lined up with the foot openings 524 at the cup mount 508, the cup 300 may be pushed downward through the opening (522 in FIG. 10) of the cup mount 508. As the separation cup 300 is pushed through the opening 522 of the cup mount 508, the base 328 of the cup 300 engages the support pad 506 and loads the biasing spring 504. The feet 337 on the base 328 of the separation cup 300 are also received into the foot recesses 530 of the rotor mount 502 as the cup 300 is pushed through the opening 522 of the cup mount 508.

Once the feet 337 on the base 328 of the separation cup 300 pass through the opening 522 of the cup mount 508, the cup 300 may be rotated in the foot recesses 530 of the rotor mount 502 such that the feet 337 on the base 328 of the cup 300 line up with the foot recesses 528 formed on the underside of the internal flanges 520 of the cup mount 508. The separation cup 300 may then be released such that the biasing spring 504 unloads and pushes the separation cup 300 upward and into the recess (526 in FIG. 10) formed on the underside of the internal flanges 520 cup mount 508. The foot recesses 528 formed on the underside of the internal flanges 520 receive the feet 337 on the base 328 of the separation cup 300. The biasing spring 504 continues to bias the support pad 506 against the base 328 of the separation cup 300, which secures the cup 300 in the recess 526 formed on the underside of the internal flanges 520 of the cup mount 508. Secured in the recess 526, the cup mount 508 may apply the rotational force provided by the rotary actuator (206 in FIG. 4A) to the separation cup 300 as mentioned above.

The separation cup 300 may be removed from the cup mounting assembly 500 by reversing the procedure: pushing down on the separation cup 300 such that the foot recesses 530 of the rotor mount 502 receive the feet 337 on the base 328 of the cup 300; rotating the cup 300 until the feet 337 on the base 328 of the cup 300 line up with the foot openings 524 of the cup mount 508, and lifting the cup 300 through the opening 522 of the cup mount 508 out of the cup mounting assembly 500.

Figure 12:
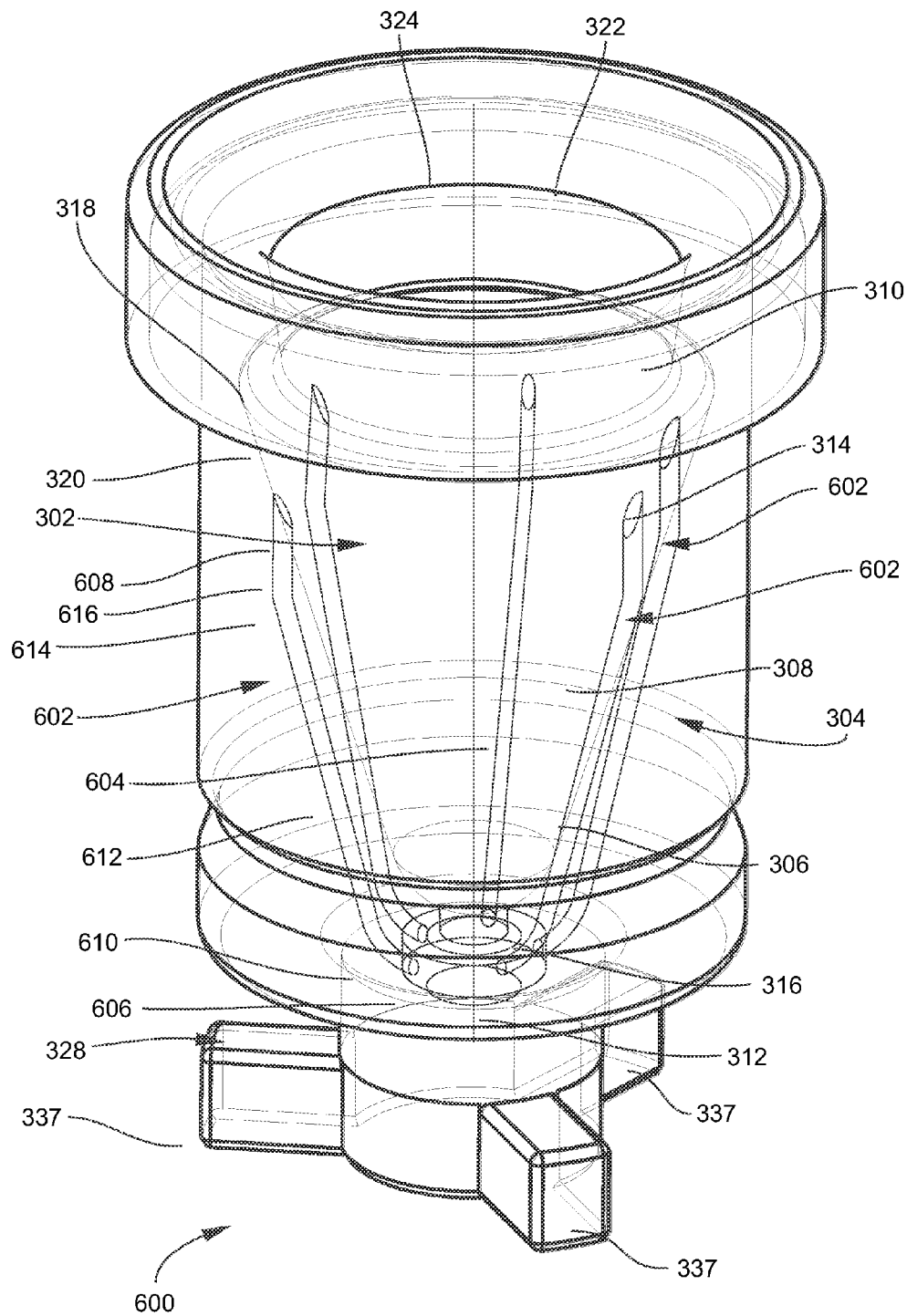
FIG. 12 is a top perspective view of an example of an alternative implementation of a separation cup.

Referring now to FIG. 12, an example of an alternative implementation of a separation cup 600 is shown. The alternative implementation of the separation cup 600 includes one or more passages 602 formed through the body 304 of the cup 600 that define flow paths from the lower end 316 of the central body region 308 to the upper end 314 of the central body region 308 near the annular shoulder trap 320. The passages 602 each include a longitudinal bore 604 formed through the body 304 of the separation cup 600 that connects a lower aperture 606 formed in the inner wall 306 near the lower end 316 of the central body region 308 to an upper aperture 608 formed in the inner wall 306 near the upper end 314 of the central body region 308 below the shoulder trap 320.

As the separation cup 600 spins, centrifugal forces drive the cell suspension towards lower apertures 606 formed in the inner wall 306 near the lower end 316 of the central body region 308. The centrifugal forces drive the cell suspension through the lower apertures 606 and into the bores 604 of the passages 602. The centrifugal forces then drive the cell suspension upwards through the bores 604 of the passages 602 and out of the upper apertures 608 below the shoulder trap 320. As the cell suspension exits the upper apertures 608, the relatively more dense material is deposited in the shoulder trap 320 while the relatively less dense material continues past the shoulder trap 320 and out of the cup 600 as described above.

As mentioned above, the cell suspension may include cells—the relatively more dense material—suspended in a media such as a buffer solution—the relatively less dense material. The passages 602 of the separation cup 600, in this alternative example, advantageously help to ensure that the cells remain immersed in the buffer solution as the cells travel upward through the passages 602 toward the shoulder trap 320.

The alternative implementation of the separation cup 600 shown by way of example in FIG. 12 includes six passages 602 from the lower end 316 to the upper end 314 of the central body region 308. The passages 602, in this example, each include a longitudinal bore 604 that connects a lower aperture 606 formed in the inner wall 306 to an upper aperture 608 formed in the inner wall 306. Also seen in FIG. 12, the passages 602, in this example, may be angled relative to the body 304 of the separation cup 600.

Additionally, the passages 602 may include different regions that define the respective flow paths. As shown by way of example in FIG. 12, a passage 602 may include a lower elbow-shaped region 610 connected to the lower aperture 606; the lower elbow-shaped region 610 leads to a slanted middle region 612; the slanted middle region 612 leads to an upper elbow-shaped region 614; the upper elbow-shaped region 614 leads to a vertical top region 616; and the vertical top region 616 is connected to the upper aperture 608.

The upper apertures 608 and lower apertures 606 may, for example, have a circular or an oval shape. Accordingly, a cross-section of a bore 604 of a passage 602 may also have a circular or oval shape. The width of the apertures 606 and 608 may be around, for example, 1 mm, and the width of the bores 604 of the passages 602 may also be around, for example, 1 mm. The passages 602 may have a length, for example, of around 40 mm.

A method for separating materials of different densities using the separation cup described above has also been developed. The method may be employed to prepare cells for use in a biological assay such as those carried out by automated high-throughput electrophysiology measurement systems. As evident from the present disclosure, the method may be automated and thus conducive for implementation with a suitable automated system such as the system 100 described above and illustrated by example in FIGS. 1 and 2.

Figure 13:
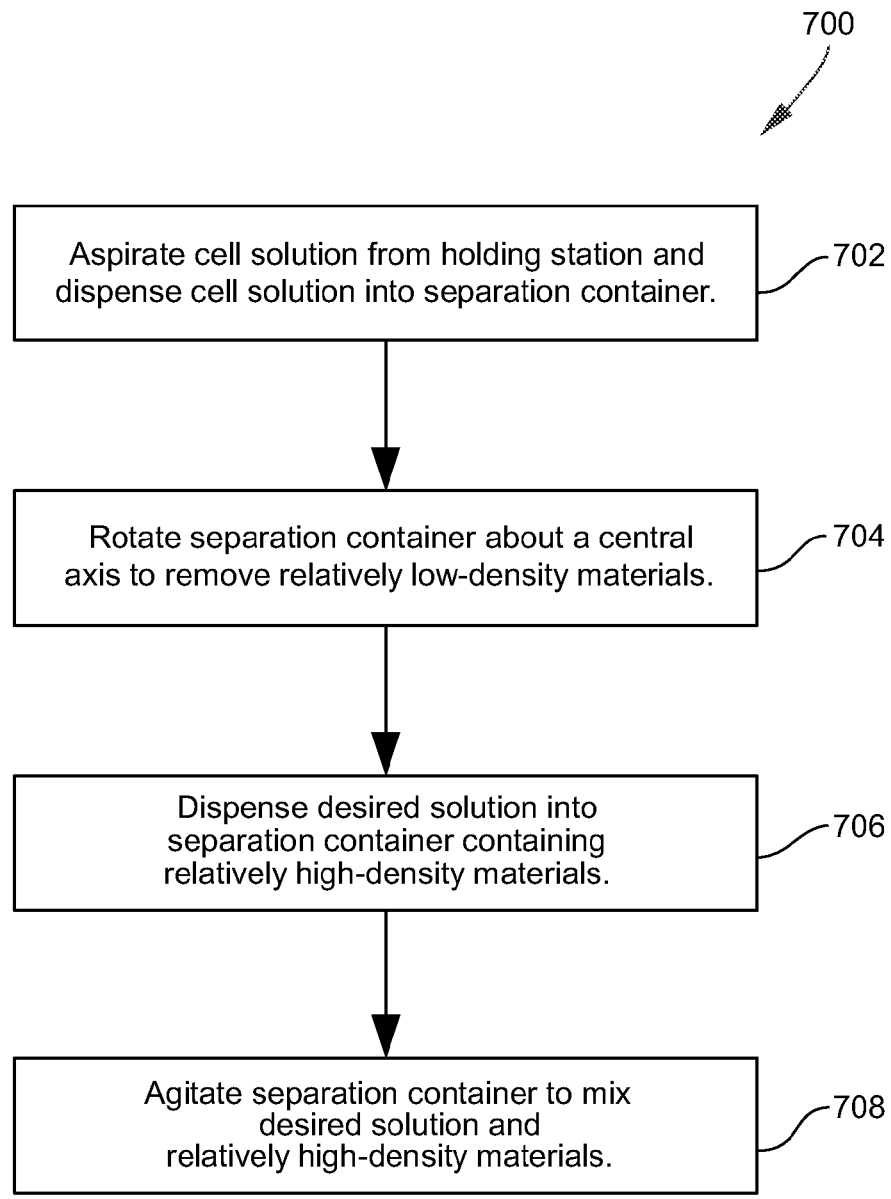
FIG. 13 is a flowchart of example method steps for automatically separating materials of different densities.

Referring to FIG. 13, a flowchart 700 of example method steps for separating materials of different densities is shown. In this example, the method is described in the context of preparing cells for a biological assay. It will be understood however, that the method may be employed in other contexts to separate other types of materials of different densities.

First, a pipettor may aspirate cell solution from a cell holding station and dispense the cell solution into the separation cup (step 702). For example, around 15 milliliters (ml) to around 30 ml of cell solution may be dispensed into the separation cup. The pipettor may dispense the cell solution into the separation cup at rate of, for example, around 100 microliters (µl) per second (s).

The separation cup may then be rotated about a central axis in order to remove the relatively low-density materials from the cup as described above (step 704). The separation cup, in this example, may be rotated at a spin speed of around 3000 rotations per minute (rpm) in order to remove the relatively low-density materials.

After the relatively low-density materials have been removed from the separation cup, the pipettor may then dispense a desired solution (e.g., wash buffer) into the cup (step 706). For example, around 20 ml to around 30 ml of desired solution may be dispensed into the separation cup. Like before, the pipettor may dispense the desired solution into the separation cup at a rate of around 100 µl/s. The pipettor may deliver the desired solution to the separation cup while the cup is still spinning.

Having delivered the desired solution to the separation cup, the cup may be agitated to remove the relatively high-density materials from the shoulder trap and place the relatively high-density materials in the desired solution (step 708). In this way, the method ensures that substantially all of the relatively high-density materials are in the desired solution.

Figure 14:
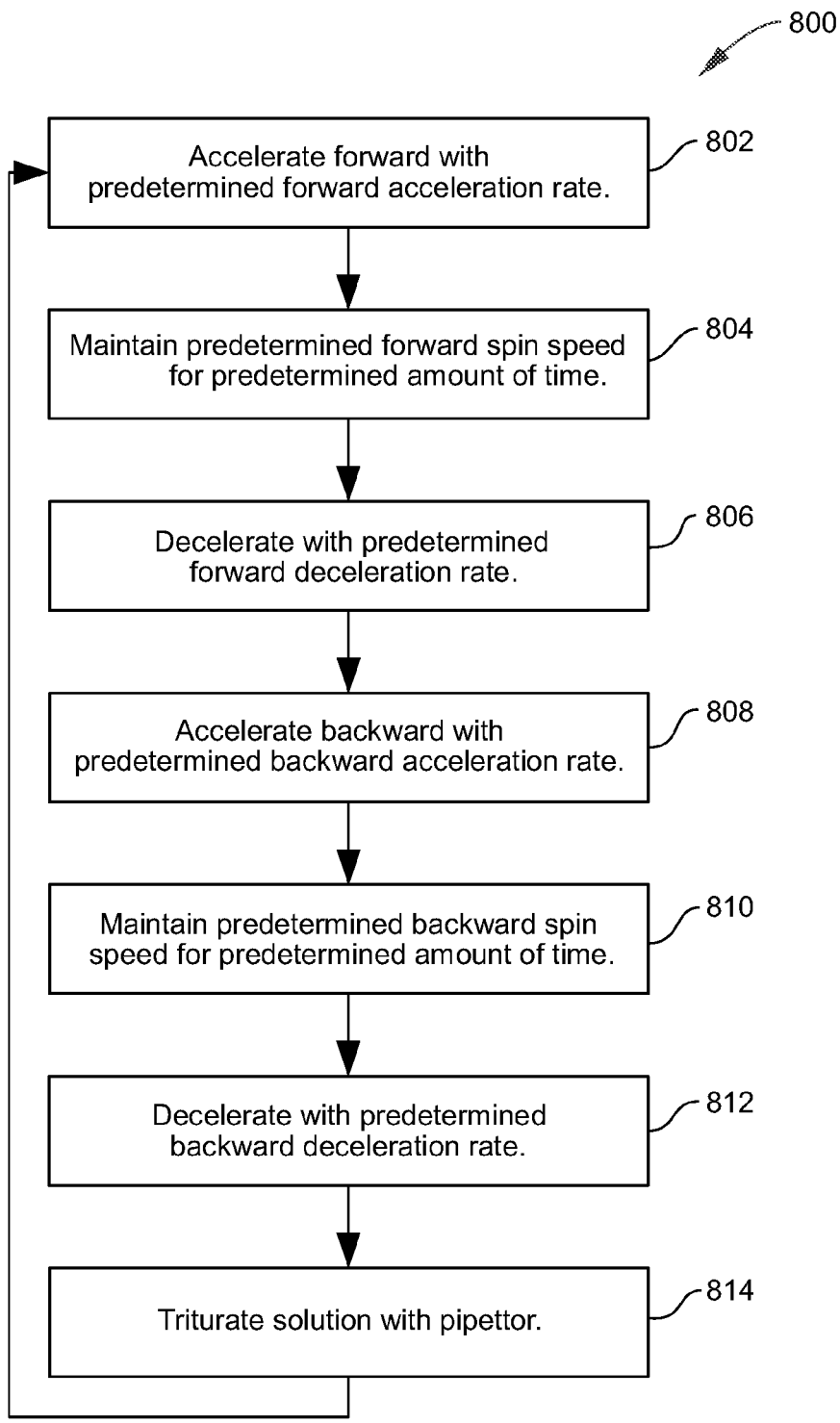
FIG. 14 is a flowchart of example method steps for automatically agitating a separation cup of an automated apparatus for separating materials of different densities.

Agitating the separation cup to mix the desired solution and the cells may involve controlling the rotational duration, direction, speed, acceleration, and deceleration. As mentioned above, the control module may control the rotary actuator when the actuator drives the rotation of the separation cup. Referring to FIG. 14, a flowchart 800 of example method steps for automatically agitating the separation cup is shown. It will be understood that any combination or subset of the agitation steps discussed below may be selectively performed to agitate the separation cup. First, the separation cup may be accelerated forward (e.g., clockwise) at a predetermined forward acceleration rate (step 802), and a predetermined forward spin speed may be maintained for a predetermined duration (step 804). After maintaining the forward spin speed, the separation cup may be decelerated at a predetermined forward deceleration rate (step 806). The predetermined forward acceleration rate may be, for example, 1000 rotations per minute (rpm) per second (s)—rpm/s; the predetermined forward spin speed may be, for example, 3000 rpm; the predetermined duration may be, for example, 100 s; and the predetermined forward deceleration rate may be, for example, 1000 rpm/s.

The separation cup may then be accelerated backward (e.g., counterclockwise) at a predetermined backward acceleration rate (step 808), and a predetermined backward spin speed may be maintained for a predetermined duration (step 810). After maintaining the backward spin speed, the separation cup may be decelerated at a predetermined backward deceleration rate (step 812). The predetermined backward acceleration rate may be, for example, 1000 rpm/s; the predetermined backward spin speed may be, for example, 3000 rpm; the predetermined duration may be, for example, 100 s; and the predetermined backward deceleration rate may be, for example, 1000 rpm/s.

After spinning the separation cup forwards and backwards as described above, the pipettor may be used to triturate the cell solution (step 814) and thereby achieve the desired level of homogeneity. Triturating the cell solution may include aspirating the cell solution from the separation cup with a pipettor and dispensing the cell solution back into the separation cup. The pipettor may aspirate and dispense the solution a predetermined number of times (e.g., ten times) when triturating the cell solution. If more uniform homogeneity is desired, then additional trituration steps may be performed.

In general, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

The foregoing description of implementations has been presented for purposes of illustration and description. It is not exhaustive and does not limit the claimed inventions to the precise form disclosed. Modifications and variations are possible in light of the above description or may be acquired from practicing the invention. The claims and their equivalents define the scope of the invention.

What is claimed is:

1. An apparatus for separating materials of different densities, the apparatus comprising:
    a separation cup having an internal cavity configured to hold media and comprising a bottom region, an opening, and a shoulder trap between the bottom region and the opening, the separation cup comprising
    an inner wall defining a central body region with an upper and a lower ends and forming therein the internal cavity of a substantially conical shape having a diameter tapering downward toward the lower end of the central body region, an interior shoulder circumscribing the upper end and defining of the central body region, the shoulder trap circumscribing the internal cavity and a neck region above the central body region, and further comprising
    one or more passages formed through from the lower end of the central body region to the upper end of the central body region; and the one or more passages each define a flow path from the lower end to the upper end of the central body region of the separation cup,
    wherein the diameter of the internal cavity increases in a downward direction through the shoulder trap; and reduces in a downward direction through the neck region,
    wherein the shoulder trap is configured such that when the separation cup is spun about a central axis, relatively more dense material in the media is collected in the shoulder trap, and relatively less dense material in the media is expelled from the separation cup through the opening; and
    a rotary actuator coupled to the separation cup and configured to spin the separation cup about a central axis of the separation cup.

2. The apparatus of claim 1 wherein:
    the separation cup further includes an opening portion above the neck region and circumscribing the neck region; and
    the opening portion flares outward away from the neck region.

3. The apparatus of claim 1 wherein the one or more passages of the separation cup each include a longitudinal bore that connects a lower aperture formed in the inner wall near the lower end of the central body region to an upper aperture formed in the inner wall near the upper end of the central body region below the shoulder trap.

4. The apparatus of claim 1 further comprising a housing that surrounds the separation cup wherein the housing includes a collection chamber that circumscribes an opening portion of the separation cup such that the collection chamber receives the relatively less dense material expelled from the separation cup when the separation cup is spun about the central axis.

5. The apparatus of claim 4 wherein a floor of the collection chamber slants towards a drain such that the relatively less dense material expelled from the separation cup is drainable away from the collection chamber.

6. The apparatus of claim 1 further comprising a mounting assembly that couples the separation cup to the rotary actuator wherein the separation cup is releasably securable within the mounting assembly.

\* \* \* \* \*